(12) United States Patent
Ballantyne et al.

(10) Patent No.: US 7,704,693 B1
(45) Date of Patent: Apr. 27, 2010

(54) AGE DETERMINATION FROM BIOLOGICAL STAINS USING MESSENGER RNA PROFILING ANALYSIS

(75) Inventors: John Ballantyne, Orlando, FL (US); Michelle Alvarez, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 290 days.

(21) Appl. No.: 11/805,994

(22) Filed: May 25, 2007

Related U.S. Application Data

(62) Division of application No. 11/232,313, filed on Sep. 21, 2005, now Pat. No. 7,276,340.

(60) Provisional application No. 60/612,233, filed on Sep. 22, 2004.

(51) Int. Cl.
*C12Q 1/68* (2006.01)

(52) U.S. Cl. .................... 435/6; 435/91.1; 435/91.2; 536/24.33

(58) Field of Classification Search ................ None
See application file for complete search history.

(56) References Cited

OTHER PUBLICATIONS

Stratagene Catlog. p. 39. 1988.*
Juusola et al. Forensic Science International vol. 135:85-96. 2003.*
Chomczynski, P. et al., "Single-step method of RNA isolation by acid guanidinium thiocyanate- phenol-chloroform extraction." (1987), *Analytical Biochemistry*, pp. 162, 156-159.
Juusola, J. and Ballantyne, J., "Messenger RNA profiling: a prototype method to Supplant conventional methods for body fluid identification."(2003), *Forensic Science International 135*, pp. 85-96.
Livak, J. and Schmittgen, T., "Analysis of Relative Gene Expression Data Using Real-Time Quantitative PCR and the $2^{-\Delta\Delta}{}_T$ Method." (2001), *Methods 25*, pp. 402-408.

* cited by examiner

*Primary Examiner*—Heather G Calamita
(74) *Attorney, Agent, or Firm*—Brian S. Steinberger; Frances Olmsted; Law Offices of Brian S. Steinberger, P.A.

(57) ABSTRACT

Reverse transcription-quantitative polymerase chain reaction (RT-qPCR) assays, systems, methods and kits for the age determination of an individual from bloodstains or samples of unknown origin. The methodology is based on gene expression profiling analysis in which novel human newborn fetal specific genes are identified by detecting the presence of appropriate messenger RNA species.

8 Claims, 14 Drawing Sheets

HBG1 acactcgcttctggaacgtctgaggttatcaataagctcctagtccagacgccatgggtcatttcacagaggaggacaaggctac tatcacaagcctgtggggcaaggtgaatgtggaagatgctggaggagaaaccctgggaaggctcctggttgtctacccatgga cccagaggttctttgacagctttggcaacctgtcctctgcctctgccatcatgggcaaccccaaagtcaaggcacatggcaagaa ggtgctgacttccttgggagatgccacaaagcacctggatgatctcaagggcacctttgcccagctgagtgaactgcactgtgac aagctgcatgtggatcctgagaacttcaagctcctgggaaatgtgctggtgaccgttttggcaatccatttcggcaaagaattcac ccctgaggtgcaggcttcctggcagaagatggtgactgcagtggccagtgccctgtcctccagataccactgagctcactgccc atgattcagagctttcaaggataggctttattctgcaagcaatacaaataataaatctattctgctgagagatcac

Figure 1

HBG2 acactcgcttctggaacgtctgaggttatcaataagctcctagtccagacgccatgggtcatttcacagaggaggacaaggctac tatcacaagcctgtggggcaaggtgaatgtggaagatgctggaggagaaaccctgggaaggctcctggttgtctacccatgga cccagaggttctttgacagctttggcaacctgtcctctgcctctgccatcatgggcaaccccaaagtcaaggcacatggcaagaa ggtgctgacttccttgggagatgccataaagcacctggatgatctcaagggcacctttgcccagctgagtgaactgcactgtgac aagctgcatgtggatcctgagaacttcaagctcctgggaaatgtgctggtgaccgttttggcaatccatttcggcaaagaattcac ccctgaggtgcaggcttcctggcagaagatggtgactggagtggccagtgccctgtcctccagataccactgagctcactgccc atgatgcagagctttcaaggataggctttattctgcaagcaatcaaataataaatctattctgctaagagatcac

Figure 2

HBG1n acactcgcttctggaacgtctgaggttatcaataagctcctagtccagacgccatgggtcatttcacagaggaggacaaggctac tatcacaagcctgtggggcaaggtgaatgtggaagatgctggaggagaaaccctgggaaggctcctggttgtctacccatgga cccagaggttctttgacagctttggcaacctgtcctctgcctctgccatcatgggcaaccccaaagtcaaggcacatggcaagaa ggtgctgacttccttgggagatgccacaaagcacctggatgattcagagctttcaaggataggctttattctgcaagcaatacaaat aataaatctattctgctgagagatcac Sequence ID 1

Figure 3

HBG2n acactcgcttctggaacgtctgaggttatcaataagctcctagtccagacgccatgggtcatttcacagaggaggacaaggctac tatcacaagcctgtggggcaaggtgaatgtggaagatgctggaggagaaaccctgggaaggctcctggttgtctacccatgga cccagaggttctttgacagctttggcaacctgtcctctgcctctgccatcatgggcaaccccaaagtcaaggcacatggcaagaa ggtgctgacttccttgggagatgccataaagcacctggatgatctcaagggcacctttgcccagctgagtgaactgcactgagct cactgcccatgatgcagagctttcaaggataggctttattctgcaagcaatcaaataataaatctattctgctaagagatcac Sequence ID 2

Figure 4

S15 ggcagtctcgcgataactgcgcaggcgcggaccaaagcgatctcttctgaggatccggcaagatggcagaagtagagcagaa
gaagaagcggaccttccgcaagttcacctaccgcggcgtggacctcgaccagctgctggacatgtcctacgagcagctgatgc
agctgtacagtgcgcgccagcggcggcggctgaaccggggcctgcggcggaagcagcactccctgctgaagcgcctgcgc
aaggccaagaaggaggcgccgcccatggagaagccggaagtggtgaagacgcacctgcgggacatgatcatcctacccga
gatggtgggcagcatggtgggcgtctacaacggcaagaccttcaaccaggtggagatcaagcccgagatgatcggccactac
ctgggcgagttctccatcacctacaagcccgtaaagcatggccggcccggcatcggggccacccactcctcccgcttcatccct
ctcaagtaatggctcagctaataaaggcgcacatgactcc Sequence ID 3

Figure 5

F 5' gaa-agc-tct-gaa-tca-tcc-agg-tg 3'

Sequence ID 4

Figure 6

6FAM-ttt-gtg-gca-tct-ccc-aag-gaa-gtc-agc MGBNFQ

Sequence ID 5

Figure 7

R 5' agt-caa-ggc-aca-tgg-caa-gaa-g 3'

Sequence ID 6

Figure 8

F 5' gca-gtg-agc-tca-gtg-cag-ttc 3'

Sequence ID 7

Figure 9

6FAM-caa-agg-tgc-cct-tga-gat-cat-cca-gg MGBNFQ

Sequence ID 8

Figure 10

R 5' ttc-ctt-ggg-aga-tgc-cat-aaa 3'

Sequence ID 9

Figure 11

F 5' cca-aag-cga-tct-ctt-ctg-agg-at 3

Sequence ID 10

Figure 12

VIC-cgg-caa-gat-ggc-aga-agt-aga-gca-gaa MGBNFQ

Sequence ID 11

Figure 13

R 5' acg-ccg-cgg-tag-gtg-aa

Sequence ID 12

Figure 14

AGE DETERMINATION FROM BIOLOGICAL STAINS USING MESSENGER RNA PROFILING ANALYSIS

This is a Divisional of application Ser. No. 11/232,313 filed Sep. 21, 2005 now U.S. Pat. No. 7,276,340 and claims the benefit of priority from U.S. Provisional Application Ser. No. 60/612,233 filed Sep. 22, 2004 the content of which is incorporated herein by reference.

FIELD OF THE INVENTION

This invention relates to a ribonucleic acid (RNA) based assay system for determining the biological age of an individual from which a body fluid originated.

SEQUENCE LISTING

Appendix A is a sequence listing of mRNA and DNA sequences identified in FIGS. 1-14, the content of Appendix A is also submitted on a compact disc and is incorporated herein by reference. Attached hereto is one compact disc containing the following files:
  SEQ. 1 provides the mRNA sequence of HBG1
  SEQ. 2 provides the mRNA sequence of HBG2
  SEQ. 3 provides the mRNA sequence of HBG1n (Seq. ID 1)
  SEQ. 4 provides the mRNA sequence of HBG2n (Seq. ID 2)
  SEQ. 5 provides the mRNA sequence of S15 (Seq. ID 3)
  SEQ. 6 provides the DNA sequence of an HBG1n primer (Seq. ID 4)
  SEQ. 7 provides the DNA sequences of an HBG1n probe (Seq. ID 5)
  SEQ. 8 provides the DNA sequences of an HBG1n primer (Seq. ID 6)
  SEQ. 9 provides the DNA sequences of an HBG2n primer (Seq. ID 7)
  SEQ. 10 provides the DNA sequences of an HBG2n probe (Seq. ID 8)
  SEQ. 11 provides the DNA sequences of an HBG2n primer (Seq. ID 9)
  SEQ. 12 provides the DNA sequences of an S15 primer (Seq. ID 10)
  SEQ. 13 provides the DNA sequences of an S15 probe (Seq. ID 11)
  SEQ. 14 provides the DNA sequences of an S15 primer (Seq. ID 12)

BACKGROUND AND PRIOR ART

It is now a routine matter for forensic scientists to obtain the genetic profile of an individual from deoxyribonucleic acid (DNA) recovered from a biological stain deposited at a crime scene. However, in certain instances where there is no developed suspect as yet or there is no match with any database sample, the DNA profile per se provides no meaningful information to investigators, with the notable exception of gender determination. To aid in these investigations another useful biometric that could provide important probative information is the biological age of an individual. For example, the ability to provide investigators with information as to whether a DNA donor is a newborn baby, an adolescent teenager or an elderly individual could be useful in certain cases, particularly those involving young children such as kidnappings or in providing additional intelligence during terrorist investigations. Currently no reliable validated molecular tests are available for age determination.

Numerous molecular theories have been investigated for their correlation with human ageing. Postulated molecular mechanisms include, inter alia, progressive damage to DNA, telomere shortening, long-lived protein glycation and reactive oxygen species (ROS)-mediated oxidative damage to macromolecules. A major downfall to these approaches is that they are characterized by the "degenerative" ageing process, whereby as individuals increase in age the amount of damage also increases, this is especially characteristic of older aged individuals. From the forensic standpoint, however, it would be useful to be able to distinguish between individuals of all age groups and this may require the detection of more subtle molecular changes. An alternate approach to age determination relies on epigenetic and developmental control of gene expression through messenger RNA (mRNA) profiling analysis. This theory of "developmental" ageing, would allow individuals to be categorized into various age groups, each correlated with a specific stage of human development.

The life-cycle of humans comprises a number of developmentally recognized stages. As the human proceeds through these developmental stages, sub-sets of the 20-50 thousand human genes will be differentially expressed. Determining the global gene expression profile (or differential mRNA gene expression profile) present in a biological stain could reveal constellations of genes whose expression is correlated with a specific age. For example, identifying fetal hemoglobin (HBG) and fetal specific regulating mRNA species, isolating pubertal and pre-pubertal hormones and receptors or assaying for DNA damage and repair factors would be indicative of newborn babies, adolescent teenagers and elderly individuals, respectively.

SUMMARY OF THE INVENTION

A primary objective of the present invention is to provide two novel newborn specific fetal hemoglobin genes.

A second objective of the present invention is to provide an mRNA based method for identifying the newborn specific genes present in a bloodstain.

A third objective of the present invention is to provide a kit for the analysis of bloodstains to determine if a particular bloodstain originated from a newborn individual.

A preferred method for identifying whether a stain contains blood of a newborn human being, includes, obtaining a sample stain consisting of a body fluid from a human being, extracting total ribonucleic acid (tRNA) from the sample stain, treating the total RNA with an enzyme, initiating a reverse-transcription (RT) reaction by treating total RNA with random decamer primers and a reverse transcriptase enzyme to produce cDNA, amplifying the cDNA using HBGv-specific and HSK primers with corresponding fluorescently labeled probes, identifying the age of the donor by determining the cycle threshold (Ct) value of a housekeeping gene (HSK) and the Ct value of the HBGv target gene, then subtracting the Ct value of the target gene, from the Ct value of the HSK gene, wherein a positive value would indicate that the blood originates from a newborn human being.

A more preferred method uses the reverse transcriptase enzyme, Moloney Murine Leukemia Virus (MMLV-RT) and has 2 variants of hemoglobin (HBG) used as primers. The 2 variants of HBG are HBG1n and HBG2n and the primers are segments of HBG1n and HBG2n. More preferably, the primers are one or more selected from the sequence ID 4, 5, 6, 7, 8, 9, 10, 11 or 12.

The preferred identifying probes fluoresce and the values are determined by finding the Ct of the HSK and the Ct of each of the variants of HBG and then subtracting the Ct of the HBGv from the Ct of the HSK, generating a dCt value. The HSK is the ribosomal protein, S15 and the age of the newborn is less than 1 week old or the age of the newborn can be less than 5 months old. More preferably, the HSK is glyceraldehyde-3-phosphate dehydrogenase (GAPDH).

The preferred extracting procedure for the total RNA uses a denaturing solution such as guanidine isothiocyanate-phenol:chloroform. Preferably, the extracted total RNA is precipitated with an organic solvent, such as, isopropanol. The preferred enzyme used to treat the extracted total RNA is deoxyribonuclease I (DNase I).

A preferred gene coding for the human newborn specific fetal hemoglobin variant is HBG1n as in SEQ ID 1 and HBG2n as in SEQ ID 2.

Another preferred gene coding for the human newborn specific fetal hemoglobin variants are HBG1n and HBG2n and polymorphisms thereof.

A preferred kit for use in determining the biological age of an individual in an unknown bloodstain, uses HBG1n and HBG2n and HSK specific primers, preferably, selected from one or more of sequence ID 4, 5, 6, 7, 8, 9, 10, 11, or 12; the preferred housekeeping gene is the ribosomal protein, S15. The preferred probes are labeled with fluorescent dyes.

Further objects and advantages of this invention will be apparent from the following detailed description and example of a presently preferred embodiment.

BRIEF DESCRIPTION OF THE FIGURES

FIG. 1 provides the mRNA sequence of HBG1
FIG. 2 provides the mRNA sequence of HBG2
FIG. 3 provides the mRNA sequence of HBG1n
FIG. 4 provides the mRNA sequence of HBG2n
FIG. 5 provides the mRNA sequence of S15
FIG. 6 provides the DNA sequence of an HBG1n primer
FIG. 7 provides the DNA sequences of an HBG1n probe
FIG. 8 provides the DNA sequences of an HBG1n primer
FIG. 9 provides the DNA sequences of an HBG2n primer
FIG. 10 provides the DNA sequences of an HBG2n probe
FIG. 11 provides the DNA sequences of an HBG2n primer
FIG. 12 provides the DNA sequences of an S15 primer
FIG. 13 provides the DNA sequences of an S15 probe
FIG. 14 provides the DNA sequences of an S15 primer

DESCRIPTION OF THE PREFERRED EMBODIMENTS

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

Below is a listing of several acronyms used herein:
DNA is deoxyribonucleic acid
Ct is cycle threshold value; it is the cycle number at which the fluorescent signal passes a pre-determined threshold.
HBG is hemoglobin
HSK is housekeeping gene
RNA is ribonucleic acid
mRNA is messenger ribonucleic acid
ROS is reactive oxygen species
RT-PCR is reverse transcription polymerase chain reaction
S15 is ribosomal protein The life-cycle of humans comprises a number of developmentally recognized stages. As the human proceeds through these developmental stages, sub-sets of the 20-50 thousand human genes will be differentially expressed. Determining the global gene expression profile (or differential mRNA gene expression profile) present in a biological stain could reveal constellations of genes whose expression is correlated with a specific age. For example, identifying fetal hemoglobin and fetal specific regulating mRNA species, isolating pubertal and pre-pubetal hormones and receptors or assaying for DNA damage and repair factors, would be indicative of newborn babies, adolescent teenagers and elderly individuals, respectively.

A clear example of age related differential gene expression involves the fetal to adult hemoglobin shift. The human beta-hemoglobin locus is located on the short arm of chromosome 11 (11p15.5), and encodes five functional beta-like globin genes: epsilon, gammaG, gammaA, delta, and beta, (hemoglobin gamma mRNA sequences, HBG1 (gammaA) and HBG2 (gammaG), are provided in FIG. 1 and FIG. 2, respectively).

The expression of embryonic hemoglobin (epsilon) commences in the yolk sac in the early stages of gestational development. During the fifth week of gestation the fetal liver, spleen and bone marrow begin to express the fetal specific gamma hemoglobin chains (gammaA and gammaG) to form the fetal hemoglobin protein. This up-regulation of gamma-globin is accompanied by a shutdown of epsilon-globin synthesis. Shortly before birth, beta-globin gene expression commences in the bone marrow, forming adult hemoglobin and inturn gamma-globin expression is down regulated. Therefore, the development of an assay which identifies gamma hemoglobin mRNA in a biological stain, would indicate that the donor of the stain is a newborn baby.

The gamma hemoglobin locus was analyzed by reverse transcription-polymerase chain reaction (RT-PCR) using two sets of highly specific primers, one designed to specifically amplify HBG1 (gammaA) and one designed for amplification of HBG2 (gammaG). In contrast to our initial hypothesis, a messenger RNA (mRNA) product corresponding to the individual HBG1 or HBG2 genes was amplified in all age groups tested. These results demonstrated that the production of gamma hemoglobin mRNA is not restricted to the fetal and newborn stages of development. Upon further investigation of these RT-PCR assays, the presence of an additional lower molecular weight amplimer was detected in only newborn individuals. These lower molecular weight products were excised, cloned, sequenced and aligned with the standard hemoglobin genes. Alignment analysis revealed these lower molecular weight amplimers to be variants of the standard gamma hemoglobin genes (HBGv) which we have termed HBG1n and HBG2n (variant gamma hemoglobin mRNA sequences HBG1n and HBG2n are provided in FIG. 3 and FIG. 4, respectively).

Based on this process the invention provides real-time PCR duplexes which are composed of one novel newborn specific fetal hemoglobin variant, HBG1n or HBG2n, whose sequences are identified as SEQUENCE ID 1 (HBG1n) (FIG. 3), SEQUENCE ID 2 (HBG2n) (FIG. 4), and one housekeeping gene (HSK), which may be the ribosomal protein, S15, glyceraldehyde-3-phosphate dehydrogenase (GAPDH) or others (example of a HSK gene sequence, S15, (SEQUENCE ID 3) (FIG. 5)). The collection of genes that are expressed within the constellation of differentiated cells that make up a body fluid is called the multicellular transcriptome. These genes comprise ubiquitously expressed housekeeping (HSK) genes, which are responsible for cell maintenance functions independent of biological age, and genes that are specifically expressed in an age dependent manner.

Fluorescent (i.e. FAM (6-carboxyfluorescein) and VIC) dye-labeled probes (i.e. minor groove binding non-fluorescent quencher (MGBNFQ)) and their corresponding unlabeled primers are incorporated into the real-time PCR (qPCR) reaction. These qPCR duplexes have been optimized to determine if a bloodstain originated from a newborn individual and are sensitive with as little as 50 pg of input RNA (into the qPCR reaction). The real-time qPCR methodology is based on determining the delta cycle threshold (dCt) values generated using the cycle threshold (Ct) of the HSK gene and the Ct of the novel hemoglobin variants (HBGv) (dCt=Ct S15–Ct HBGv). A positive dCt value would indicate a newborn origin; in contrast a negative dCt value would be obtained with all other ages.

An mRNA based approach for age determination, such as the real time PCR assays described above, could allow the facile identification of the newborn specific genes present in a bloodstain and could rapidly become a validated molecular test for newborn specific age determination.

As an example, the assay of the invention can be performed in two fashions: one in which the newborn is identified as less than 1 week old; the other as less than 5 months old, depending on the amount of material used.

The following example provides further explanation of the present invention.

Example 1

Figure 14:
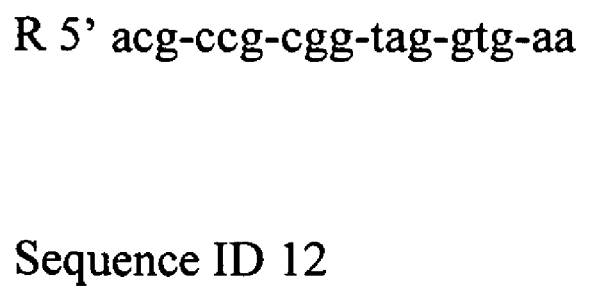

For RNA isolation, total RNA is extracted from a bloodstain using a denaturing solution, composed of guanidine isothiocyanate, the RNA is isolated with acid phenol:chloroform and precipitated with isopropanol and GlycoBlue™ glycogen carrier (from Ambion Inc., Austin, Tex.). The RNA is centrifuged and the pellet is washed once with a 75% ethanol/25% DEPC-treated water solution. The pellet is dried, re-solubilized and stored in an RNAsecure Resuspension Solution (Ambion Inc., Austin, Tex.). Next, the extracted total RNA is treated with an enzyme, deoxyribonuclease I (TURBO™ DNase (RNase-Free)) (Ambion Inc., Austin, Tex.), quantitated using the unsymmetrical cyanine dye RiboGreen® (Molecular Probes, Eugene, Oreg.) and then reverse-transcribed using fifty micromolar random decamers as the first strand primer, producing complementary DNA (cDNA). The Moloney Murine Leukemia Virus-Reverse Transcriptase enzyme (MMLV-RT) from Ambion Inc., Austin, Tex., was used in this case. Finally, the cDNA is amplified using housekeeping and newborn gene-specific primers (as exemplified in FIGS. 6-14).

Based on the above extraction and purification technique, duplex real-time PCR assays using in this case the Taqman® Universal PCR Master Mix in the 7000 Sequence detection System from Applied Biosystems, Foster City, Calif., and standard cycling conditions such as: Step 1: 1 cycle of 50 degrees C., for 2:00 minutes; Step 2: 1 cycle of 95 degrees C., for 10:00 minutes; Step 3: 40-50 cycles of 95 degrees C., for 0:15 seconds and 60 degrees C., for 1:00 minute; wherein data is collected at stage 3, step 2 (60 degrees C., for 1:00) were developed which can definitively identify newborn RNA. These duplex reactions are composed of one of the two novel variant forms of newborn gamma hemoglobin (HBGv), HBG1n or HBG2n, and a housekeeping (HSK) gene, the ribosomal protein, S15 and have been optimized for the detection of newborn individuals from bloodstains. The methodology is based on gene expression profiling analysis in which the HBGv genes are identified by detecting the presence of appropriate mRNA species. The gene-specific primers are incorporated with fluorescently labeled probes (i.e. FAM and VIC) into a single multiplexed quantitative polymerase chain reaction (qPCR). The mRNA is amplified and this amplification is detected by determining the fluorescent emission of the dye-labeled probe.

Example 2

In an assay of the invention which identifies newborns that are from 1 hour to 1 week in biological age one may proceed as Example 1 above using:

HBG1n 50 nanomolar of each primer (Forward and Reverse)
250 nanomolar of the probe HBG2n 50 nanomolar of each primer (Forward and Reverse)
250 nanomolar of the probe

S15

900 nanomolar of each primer (Forward and Reverse)
250 nanomolar of the probe

Example 3

In an assay of the invention which identifies newborns that are from 1 hour to 5 months in biological age one may proceed as in Example 1 above using:

HBG1n 100 nanomolar of each primer (Forward and Reverse)
250 nanomolar of the probe HBG2n 50 nanomolar of each primer (Forward and Reverse)
250 nanomolar of the probe

S15

600 nanomolar of each primer (Forward and Reverse)
250 nanomolar of the probe

Example 4

The cycle threshold (Ct) values obtained are used to determine the delta Ct (dCt) for that particular sample. The equation for dCt calculation is:

$$Ct(S15)-Ct(HBG1n)=dCt$$

$$Ct(S15)-Ct(HBG2n)=dCt$$

If the dCt value is positive then the sample originated from a newborn.

If the dCt value is negative then the sample originated from an age other than newborn.

If no Ct value is generated with the newborn genes (HBG1n or HBG2n) the sample is given a Ct value of 40.000 (the maximum number of cycles), for that particular gene. If no Ct value is generated with the housekeeping gene (S15) than the assay must be repeated.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. An isolated gene coding for the human newborn specific fetal hemoglobin variant HBG1n as in SEQ ID3.

2. An isolated gene coding for the human newborn specific fetal hemoglobin variant HBG2n as in SEQ ID 4.

3. A kit for use in determining the biological age of an individual in an unknown bloodstain, comprising HBG1n and HBG2n and HSK specific primers and probes wherein the primers are selected from the group consisting of one or more of SEQ ID 6, and 9.

4. A kit, as in claim 3, wherein said housekeeping gene is the ribosomal protein S15.

5. A kit, as in claim 3, wherein said probes are selected from the group consisting of one or more of Sequence ID 7 and Sequence ID10.

6. A kit, as in claim 3, wherein said probes are labeled with fluorescent dyes.

7. An isolated forward primer for the human newborn specific fetal hemoglobin variant HBG1n as in SEQ ID 6.

8. An isolated forward primer for the human newborn specific fetal hemoglobin variant HBG2n as in SEQ ID 9.

* * * * *

UNITED STATES PATENT AND TRADEMARK OFFICE
CERTIFICATE OF CORRECTION

| | |
|---|---|
| PATENT NO. | : 7,704,693 B1 |
| APPLICATION NO. | : 11/805994 |
| DATED | : April 27, 2010 |
| INVENTOR(S) | : John Ballantyne |

It is certified that error appears in the above-identified patent and that said Letters Patent is hereby corrected as shown below:

Col. 1, Line 4, Insert:

--STATEMENT REGARDING FEDERALLY SPONSORED RESEARCH OR DEVELOPMENT

This subject invention was made with government support under Technical Support Working Group on Counter Terrorism (TSWG), federal contract number TSWG Task IS-FO-159. The government has certain rights in this invention.--

Signed and Sealed this
First Day of March, 2011

David J. Kappos
*Director of the United States Patent and Trademark Office*

SEQUENCE LISTING

<160> NUMBER OF SEQ ID NOS: 14

<210> SEQ ID NO 1
<211> LENGTH: 584
<212> TYPE: DNA
<213> ORGANISM: HBG1

<400> SEQUENCE: 1

```
acactcgctt ctggaacgtc tgaggttatc aataagctcc tagtccagac gccatgggtc     60
atttcacaga ggaggacaag gctactatca caagcctgtg gggcaaggtg aatgtggaag    120
atgctggagg agaaaccctg ggaaggctcc tggttgtcta cccatggacc cagaggttct    180
ttgacagctt tggcaacctg tcctctgcct ctgccatcat gggcaacccc aaagtcaagg    240
cacatggcaa gaaggtgctg acttccttgg gagatgccac aaagcacctg gatgatctca    300
agggcacctt tgcccagctg agtgaactgc actgtgacaa gctgcatgtg gatcctgaga    360
acttcaagct cctgggaaat gtgctggtga ccgttttggc aatccatttc ggcaaagaat    420
tcacccctga ggtgcaggct tcctggcaga agatggtgac tgcagtggcc agtgccctgt    480
cctccagata ccactgagct cactgcccat gattcagagc tttcaaggat aggctttatt    540
ctgcaagcaa tacaaataat aaatctattc tgctgagaga tcac                     584
```

<210> SEQ ID NO 2
<211> LENGTH: 583
<212> TYPE: DNA
<213> ORGANISM: HGB2

<400> SEQUENCE: 2

```
acactcgctt ctggaacgtc tgaggttatc aataagctcc tagtccagac gccatgggtc     60
atttcacaga ggaggacaag gctactatca caagcctgtg gggcaaggtg aatgtggaag    120
atgctggagg agaaaccctg ggaaggctcc tggttgtcta cccatggacc cagaggttct    180
ttgacagctt tggcaacctg tcctctgcct ctgccatcat gggcaacccc aaagtcaagg    240
cacatggcaa gaaggtgctg acttccttgg gagatgccat aaagcacctg gatgatctca    300
agggcacctt tgcccagctg agtgaactgc actgtgacaa gctgcatgtg gatcctgaga    360
acttcaagct cctgggaaat gtgctggtga ccgttttggc aatccatttc ggcaaagaat    420
tcacccctga ggtgcaggct tcctggcaga agatggtgac tggagtggcc agtgccctgt    480
cctccagata ccactgagct cactgcccat gatgcagagc tttcaaggat aggctttatt    540
ctgcaagcaa tcaaataata aatctattct gctaagagat cac                      583
```

<210> SEQ ID NO 3
<211> LENGTH: 367
<212> TYPE: DNA
<213> ORGANISM: HBG1n

<400> SEQUENCE: 3

```
acactcgctt ctggaacgtc tgaggttatc aataagctcc tagtccagac gccatgggtc     60
atttcacaga ggaggacaag gctactatca caagcctgtg gggcaaggtg aatgtggaag    120
atgctggagg agaaaccctg ggaaggctcc tggttgtcta cccatggacc cagaggttct    180
```

```
ttgacagctt tggcaacctg tcctctgcct ctgccatcat gggcaacccc aaagtcaagg    240
cacatggcaa gaaggtgctg acttccttgg gagatgccac aaagcacctg gatgattcag    300
agctttcaag gataggcttt attctgcaag caatacaaat aataaatcta ttctgctgag    360
agatcac                                                              367

<210> SEQ ID NO 4
<211> LENGTH: 421
<212> TYPE: DNA
<213> ORGANISM: HBG2n

<400> SEQUENCE: 4
acactcgctt ctggaacgtc tgaggttatc aataagctcc tagtccagac gccatgggtc     60
atttcacaga ggaggacaag gctactatca caagcctgtg gggcaaggtg aatgtggaag    120
atgctggagg agaaaccctg ggaaggctcc tggttgtcta cccatggacc cagaggttct    180
ttgacagctt tggcaacctg tcctctgcct ctgccatcat gggcaacccc aaagtcaagg    240
cacatggcaa gaaggtgctg acttccttgg gagatgccat aaagcacctg gatgatctca    300
agggcacctt tgcccagctg agtgaactgc actgagctca ctgcccatga tgcagagctt    360
tcaaggatag gctttattct gcaagcaatc aaataataaa tctattctgc taagagatca    420
c                                                                    421

<210> SEQ ID NO 5
<211> LENGTH: 531
<212> TYPE: DNA
<213> ORGANISM: S15

<400> SEQUENCE: 5
ggcagtctcg cgataactgc gcaggcgcgg accaaagcga tctcttctga ggatccggca     60
agatggcaga gtagagcag aagaagaagc ggaccttccg caagttcacc taccgcggcg    120
tggacctcga ccagctgctg gacatgtcct acgagcagct gatgcagctg tacagtgcgc    180
gccagcggcg gcggctgaac cggggcctgc ggcggaagca gcactccctg ctgaagcgcc    240
tgcgcaaggc caagaaggag gcgccgccca tggagaagcc ggaagtggtg aagacgcacc    300
tgcgggacat gatcatccta cccgagatgg tgggcagcat ggtgggcgtc tacaacggca    360
agaccttcaa ccaggtggag atcaagcccg agatgatcgg ccactacctg gcgagttct    420 ccatcaccta caagcccgta agcatggccg gcccggcat cggggccacc cactcctccc    480
gcttcatccc tctcaagtaa tggctcagct aataaaggcg cacatgactc c             531

<210> SEQ ID NO 6
<211> LENGTH: 23
<212> TYPE: DNA
<213> ORGANISM: HBG1n

<400> SEQUENCE: 6
gaaagctctg aatcatccag gtg                                             23

<210> SEQ ID NO 7
<211> LENGTH: 27
<212> TYPE: DNA
<213> ORGANISM: HBG1n

<400> SEQUENCE: 7
tttgtggcat ctcccaagga agtcagc                                         27
```

```
<210> SEQ ID NO 8
<211> LENGTH: 22
<212> TYPE: DNA
<213> ORGANISM: HBG1n

<400> SEQUENCE: 8
agtcaaggca catggcaaga ag                                              22

<210> SEQ ID NO 9
<211> LENGTH: 21
<212> TYPE: DNA
<213> ORGANISM: HBG2n

<400> SEQUENCE: 9
gcagtgagct cagtgcagtt c                                               21

<210> SEQ ID NO 10
<211> LENGTH: 26
<212> TYPE: DNA
<213> ORGANISM: HBG2n

<400> SEQUENCE: 10
caaaggtgcc cttgagatca tccagg                                          26

<210> SEQ ID NO 11
<211> LENGTH: 21
<212> TYPE: DNA
<213> ORGANISM: HBG2n

<400> SEQUENCE: 11
ttccttggga gatgccataa a                                               21

<210> SEQ ID NO 12
<211> LENGTH: 23
<212> TYPE: DNA
<213> ORGANISM: S15

<400> SEQUENCE: 12
ccaaagcgat ctcttctgag gat                                             23

<210> SEQ ID NO 13
<211> LENGTH: 27
<212> TYPE: DNA
<213> ORGANISM: S15

<400> SEQUENCE: 13
cggcaagatg gcagaagtag agcagaa                                         27

<210> SEQ ID NO 14
<211> LENGTH: 17
<212> TYPE: DNA
<213> ORGANISM: S15

<400> SEQUENCE: 14
acgccgcggt aggtgaa                                                    17
```